(12) United States Patent
Iwami et al.

(10) Patent No.: US 7,278,973 B2
(45) Date of Patent: Oct. 9, 2007

(54) GUIDE WIRE

(75) Inventors: Jun Iwami, Shizuoka (JP); Noriyuki Tamai, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 442 days.

(21) Appl. No.: 10/395,222

(22) Filed: Mar. 25, 2003

(65) Prior Publication Data
US 2003/0229298 A1    Dec. 11, 2003

(30) Foreign Application Priority Data
Mar. 25, 2002   (JP)   ............... 2002-082997
Dec. 18, 2002   (JP)   ............... 2002-367390

(51) Int. Cl.
*A61B 5/00*   (2006.01)
*A61M 25/00*   (2006.01)

(52) U.S. Cl. .................................................. 600/585
(58) Field of Classification Search ............... 600/585, 600/434; 604/529, 528
See application file for complete search history.

(56) References Cited

U.S. PATENT DOCUMENTS

| | | |
|---|---|---|
| 4,951,686 A | 8/1990 | Herlitze |
| 5,084,022 A | 1/1992 | Claude |
| 5,379,779 A | 1/1995 | Rowland et al. |
| 5,452,726 A | 9/1995 | Burmeister et al. |
| 5,772,609 A | 6/1998 | Nguyen et al. |
| 5,797,857 A | 8/1998 | Obitsu |
| 5,811,369 A | 9/1998 | Nagai et al. |
| 5,836,893 A | 11/1998 | Urick |
| 5,919,170 A | 7/1999 | Woessner |
| 5,928,842 A * | 7/1999 | Shinmoto et al. ........... 430/346 |
| 5,951,494 A * | 9/1999 | Wang et al. ................ 600/585 |
| 6,022,905 A | 2/2000 | Harris et al. |

(Continued)

FOREIGN PATENT DOCUMENTS

EP    0 407 965 A1    1/1991

(Continued)

OTHER PUBLICATIONS

Chuck Bosnos et al., "Laser Marking Medical Devices and Packaging," *Medical Device & Diagnostic Industry Magazine, MDDI Article Index*, Feb. 1998, 14 pages.

*Primary Examiner*—Max F. Hindenburg
*Assistant Examiner*—Jonathan Foreman
(74) *Attorney, Agent, or Firm*—Buchanan Ingersoll & Rooney PC

(57) ABSTRACT

A guide wire is configured to have a less lossy marker formed at a desired position and providing a relatively high degree of contrastability under X-ray fluoroscopic guidance or the like. The guide wire includes a linear core member, a resin layer covering a main body portion of the core member, and a contrasting portion covering the distal end portion of the core member. The resin layer contains a color developing agent which develops color by laser light irradiation, and a contrast agent composed of a metal oxide powder. The contrasting portion is made from a resin containing a contrast agent composed of a metal powder and has a contrasting function higher than the resin layer. A visible marker is formed on the outer surface of the resin layer through color development of the color developing agent by irradiating the surface of the resin layer with laser light.

21 Claims, 9 Drawing Sheets

U.S. PATENT DOCUMENTS

| | | | |
|---|---|---|---|
| 6,036,682 A * | 3/2000 | Lange et al. | 604/529 |
| 6,050,958 A * | 4/2000 | Dickinson et al. | 600/585 |
| 6,187,390 B1 * | 2/2001 | Seeger et al. | 427/555 |
| 6,210,396 B1 * | 4/2001 | MacDonald et al. | 604/529 |
| 6,409,682 B1 | 6/2002 | Burmeister et al. | |
| 6,613,002 B1 * | 9/2003 | Clark et al. | 600/593 |
| 2001/0009980 A1 | 7/2001 | Richardson et al. | |
| 2002/0087098 A1 | 7/2002 | Iwami et al. | |

FOREIGN PATENT DOCUMENTS

| | | |
|---|---|---|
| EP | 0 669 365 A1 | 8/1995 |
| EP | 1 203 595 A1 | 5/2002 |
| JP | 4-9162 A | 1/1992 |
| JP | 4-108556 U | 9/1992 |
| JP | 6-63054 U | 9/1994 |
| JP | 2001-46508 A | 2/2001 |

\* cited by examiner

F I G. 3
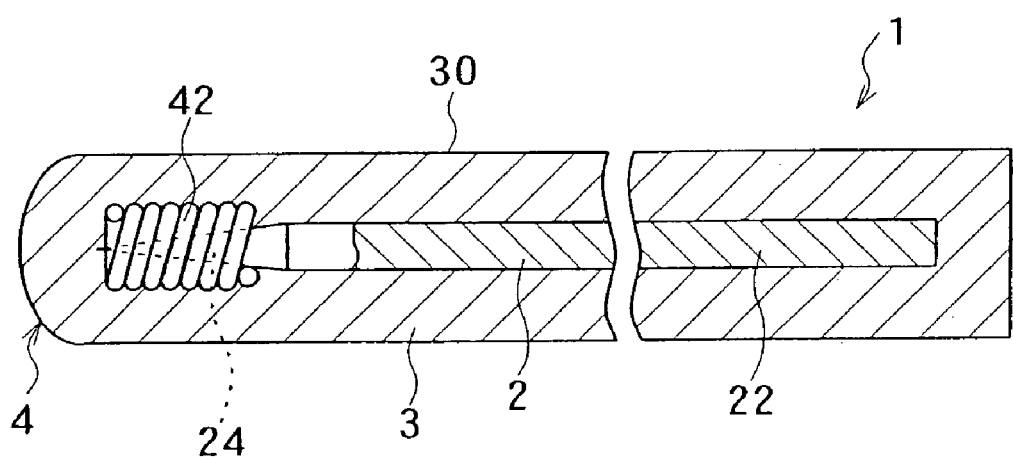

GUIDE WIRE

This application is based on and claims priority under 35 U.S.C. § 119 with respect to Japanese Application No. 2002-82997 filed on Mar. 25, 2002 and Japanese Application No. 2002-367390 filed on Dec. 18, 2002, the entire content of both of which is incorporated herein by reference.

FIELD OF THE INVENTION

The present invention generally relates to a guide wire. More particularly, the present invention pertains to a transendoscopic guide wire adapted to be inserted in a living body by way of an endoscope.

BACKGROUND OF THE INVENTION

In the observation and treatment of a biological lumen or the like using an endoscope, a guide wire is employed to introduce the endoscope or a catheter inserted in a lumen of the endoscope to a specific position in the biological lumen or the like.

During insertion of a guide wire, if the guide wire is monochromatic, it is difficult to confirm the axial movement of the guide wire. It is thus preferable to provide a mark on the surface of the guide wire indicating the position or the like. In this regard, various methods have been proposed for providing marks on guide wires.

For example, one known method generally discussed in U.S. Pat. No. 5,379,779 involves preparing a hollow tube made from polytetrafluoroethylene (sold under the trademark Teflon®) with a plurality of colored stripe patterns, inserting a core member of a guide wire in the hollow tube, and bonding the hollow tube to the core member by heat shrink.

However, this method using a hollow tube has disadvantages in that because the mark (colored stripe patterns) is provided simultaneously with the formation of the guide wire, it is difficult to provide the mark at a desired position. Also, there are limitations with respect to the degree of freedom in the shape and width of the mark.

A method of forming a mark on a guide wire by printing is also known and generally discussed in Japanese Utility Model Laid-open No. Hei 4-108556. A method which utilizes printing, however, has disadvantages in that because the ink has little or no resistance against solvent, it is difficult to coat the surface of a guide wire with a lubricating layer made from a hydrophilic polymer or the like after formation of the mark on the surface of the guide wire. In addition, it is difficult to form the mark on a curved surface of the guide wire, and the ink takes a relatively long time to dry and is liable to flow in a living body during use of the guide wire.

A method for addressing these shortcomings is generally discussed in Japanese Utility Model Laid-open No. Hei 4-63054 and involves providing a coating layer made from a transparent fluorocarbon resin on the surface of a guide wire after a mark is provided on the surface of the guide wire by printing.

This improved method, however, has its own disadvantages because it requires additional steps of drying ink and forming the coating layer, thereby complicating the production process. In addition, there is a limitation in design in that only a transparent resin is used for forming the coating layer.

U.S. Pat. No. 4,951,686 discusses a method of heating a color mark formation portion of a catheter introducing wire (guide wire) made from steel at a temperature at which a temper color appears. This method of forming a temper color mark on the surface of the guide wire by heating is disadvantageous in that it can be applied only to a catheter introducing wire made from a steel material. For example, the physical properties of a superelastic alloy (Ni—Ti alloy) generally used as the material of a core member of a guide wire are liable to be changed by heat-treatment such as heating and so this method is not well suited to being applied to a guide wire having a core member made from such a superelastic alloy. U.S. Pat. No. 4,951,686 also describes a method of forming a mark by stamping or irradiation with laser light. However, the formation of a mark by stamping is not well suited to providing a raised marked portion while the formation of a mark by irradiation with laser light is not well suited to providing a recessed marked portion.

At the time of insertion of a guide wire or a catheter to a specific position in a biological lumen or the like via an endoscope, it is oftentimes necessary to overpass the range observable by the endoscope and further advance in a peripheral lumen. In this case, to diagnose such a peripheral lumen, an X-ray contrast agent is injected into the lumen, with the diameter and the shape of the lumen being observed by irradiating the lumen with X-rays. A guide wire to be inserted in a lumen contains an X-ray contrast agent, particularly at the distal end, in order to confirm the position of the distal end.

A guide wire to be inserted via an endoscope, which has a mark visible by an endoscope and also containing an X-ray contrast agent, is known from U.S. Pat. No. 5,379,779 and Japanese Patent Laid-Open No. 2001-46508. According to the method described in Japanese Patent Laid-Open No. 2001-46508, a mark is formed by inserting a core member in a tube having a previously formed pattern, and bonding the tube to the core member by heat shrink, or by coating the core member with a paint. This method thus has similar problems to those mentioned above in connection with the methods discussed in U.S. Pat. No. 5,379,779 and Japanese Utility Model Laid-open No. Hei 4-108556.

A need thus exists for a guide wire having a less lossy marker (a relatively indelible marker less susceptible to peeling, less loss due to dissolution and less fading) possessing the desired size and shape at a desired position while ensuring a relatively high contrastability under X-ray fluoroscopic guidance or the like, with the sharpness of the marker being relatively ensured by suppressing heat generation at the time of formation of the marker.

SUMMARY OF THE INVENTION

According to one aspect, a guide wire includes a linear core member and a resin layer positioned about at least part of the core member, with the resin layer containing a color developing agent allowed to develop a color by irradiation with laser light. A color developing portion is provided on the resin layer and is preferably formed by color development of the color developing agent. In addition, the resin layer contains a contrast agent composed of a powder of a metal oxide.

The guide wire preferably further includes a contrasting portion having a contrasting function higher than that of the resin layer, with the contrasting portion being formed at the distal end portion of the core member.

According to another aspect, a guide wire includes a linear core member and a cover layer positioned about the outer periphery of the core member. The main body portion is comprised of a main body portion possessing a nearly constant outer diameter and a taper portion having an outer diameter gradually reduced in the direction toward the distal end, with the taper portion being provided on the distal end side from the main body portion. The cover layer is comprised of a first resin layer containing a color developing agent and a contrast agent composed of a powder of a metal oxide, and a second resin layer positioned on the distal end side from the first resin layer. A color developing portion is provided on the first resin layer, with the color developing portion being formed by color development of the color developing agent. The distal end portion of the first resin layer overlaps the proximal end portion of the second resin layer to form an overlapping portion.

At least a part of the overlapping portion is preferably positioned on the taper portion of the core member. In addition, at the overlapping portion, the thickness of the first resin layer is preferably gradually decreased in the direction toward the distal end, and the thickness of the second resin layer is preferably gradually increased in the direction toward the distal end.

In accordance with a third aspect, a guide wire includes a linear core member and a cover layer positioned about the outer periphery of the main body portion. The linear core member is comprised of a main body portion possessing a nearly constant outer diameter and a taper portion possessing an outer diameter gradually reduced in the direction toward the distal end, with the taper portion being provided on the distal end side from the main body portion. The cover layer is comprised of a first resin layer containing a color developing agent and a contrast agent composed of a powder of a metal oxide, and a second resin layer having at least part positioned between the first resin layer and the core member. A color developing portion is provided on the first resin layer and is formed by color development of the color developing agent.

The metal oxide is preferably at least one kind selected from a group consisting of barium sulfate, barium carbonate, and bismuth oxide. In addition, the average particle size of the contrast agent is preferably in a range of 1 to 10 μm.

The content of the color developing agent in the resin layer, for example the first resin layer, is preferably in a range of 0.01 to 10 wt %. The content of the contrast agent in the resin layer, for example the first resin layer, is preferably in a range of 30 to 80 wt %.

The contrasting portion is preferably made from a resin containing a contrast agent composed of a metal powder, the metal powder is preferably a powder of tungsten or a noble metal, and the contrasting portion is preferably formed of a metal member. It is preferable that the metal member be formed into a ring shape or coil shape.

The distal end portion of the core member is preferably formed into such a taper shape that the outer diameter is gradually reduced in the direction toward the distal end.

The color developing portion is preferably a visible marker having a portion formed into a spiral shape or an annular shape.

At the overlapping portion, it is preferable that the thickness of the first resin layer gradually decreases in the direction toward the distal end, while the thickness of the second resin layer gradually increases in the direction toward the distal end. Additionally, the proximal end of the overlapping portion is preferably positioned in the vicinity of the proximal end of the taper portion, and the distal end of the overlapped portion is preferably positioned on a portion of the taper portion. Other possible preferred configurations include the proximal end of the overlapping portion being positioned on the distal end side from the proximal end of the taper portion while the distal end of the overlapping portion is positioned on a portion of the taper portion, and the proximal end of the overlapping portion being positioned on the proximal end side from the proximal end of the taper portion while the distal end of the overlapping portion is positioned on a portion of the taper portion.

At the overlapping portion, the first resin layer can be covered with the second resin layer. Alternatively, the second resin layer can be covered with the first resin layer in the overlapping portion.

The boundary between the first resin layer and the second resin layer preferably substantially forms a continuous outer surface to the cover layer substantially without a stepped portion.

The taper portion is preferably configured with a portion whose taper angle changes.

At least a part of the second resin layer preferably forms the contrasting portion. In this case, the second resin layer preferably contains the contrast agent and has a contrasting function higher than that of the first resin layer. The content of the contrast agent in the first resin layer is preferably larger than that of the contrast agent in the second resin layer. A part of or the entire contrast agent in the second resin layer is preferably a contrast agent composed of a metal powder.

The core member preferably has, at the distal end of the taper portion, a small-diameter portion or a small-piece portion.

The core member can preferably be formed by coupling two or more kinds of core member parts (wire parts) made from different materials to each other.

The outer surface of the guide wire is preferably coated with a hydrophilic lubricating coating and/or a hydrophobic lubricating coating. The distal end side of the guide wire can be coated with a hydrophilic lubricating coating while the proximal end side of the guide wire is coated with a hydrophobic lubricating coating, wherein the boundary between the coatings is located at a position spaced 30 to 500 mm from the distal end of the guide wire.

According to preferred aspects of the guide wire, because the guide wire has the color developing portion such as a marker while ensuring a relatively high contrastability under, for example, X-ray fluoroscopic guidance, the position or the like of the guide wire can be confirmed in a living body by observation through, for example, an endoscope. In particular, because the color developing portion can be configured as the visible marker having a desired shape and size formed at a desired position, it is possible to achieve improved visibility of the color developing portion. The visible marker representative of the color developing exhibits relatively clear color difference and brightness (contrast) with the matrix of the resin layer (cover layer) covering the core member, and is less susceptible to peeling, less lost due to dissolution, and less fading. Also, such a marker possessing relatively excellent visibility can be formed without the occurrence of substantial projection and recess.

Because the contrast agent contained in the resin layer, for example the first resin layer, is composed of a powder of a metal oxide, at the time of forming the color developing portion on the surface of the resin layer by irradiating the surface with laser light, the contrast agent is less altered (oxidized) or deteriorated, and generally does not cause any spark or the like. Accordingly, the degree of freedom in selection of the kind and irradiation intensity (energy) of laser light can be broadened to better clarify the color development of the color developing agent, thus improving the visibility of the marker.

The guide wire is preferably configured so that at the distal end portion of the guide wire, the flexibility is gradually increased in the direction toward the distal end. As a result, the distal end of the guide wire can be flexibly curved so that it is possible to inhibit or prevent the occurrence of kinking (sharp bending) of the guide wire, thus improving the operation and safety at the time of insertion of the guide wire in a living body via a catheter or the like.

Even if a bending force or torsional force is repeatedly applied to the guide wire, peeling of the cover layer and/or peeling of one of the first and second resin layers from the other at the overlapping portion is inhibited. In particular, in the case where the overlapping portion is configured such that the thickness of the first resin layer is gradually decreased in the direction toward the distal end and the thickness of the second resin layer is gradually increased in the direction toward the distal end, the change in flexibility of the guide wire at the overlapping portion and its neighboring region is smoothened and the adhesion between the first resin layer and the second resin layer is increased.

In the case where a contrastability is imparted to the distal end portion of the guide wire, or a contrastability higher than that of another portion is imparted to the distal end of the guide wire, the position of the guide wire in a living body, particularly the position of the distal end of the guide wire in a living body, can be relatively easily confirmed from outside of the living body.

With the outer surface of the guide wire coated with the hydrophilic lubricating coating and/or the hydrophobic lubricating coating, it is possible to more smoothly and safely perform operation of the guide wire at the time of insertion or removal of the guide wire.

BRIEF DESCRIPTION OF THE DRAWING FIGURES

The foregoing and additional features and characteristics of the present invention will become more apparent from the following detailed description considered with reference to the accompanying drawing figures in which like reference numerals designate like elements.

FIG. 3 is a vertical cross-sectional view of a second embodiment of the guide wire of the present invention.

DETAILED DESCRIPTION

Figure 1:
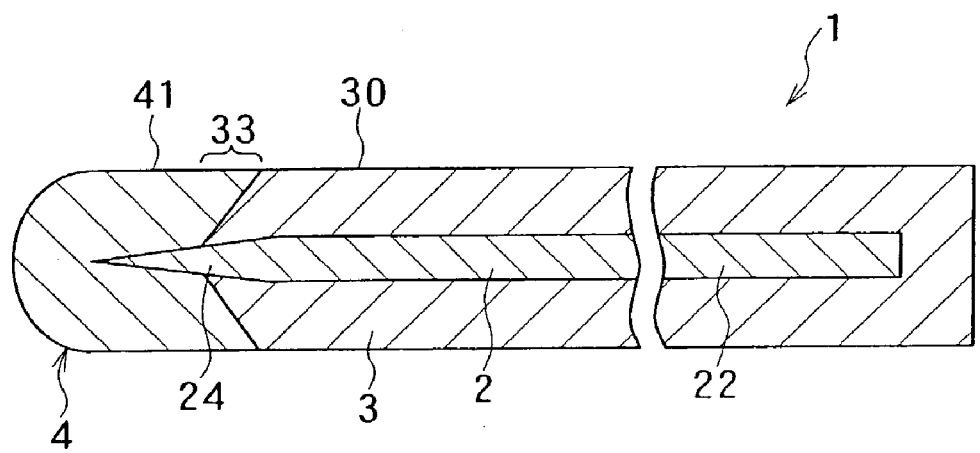
FIG. 1 is a vertical cross-sectional view of a first embodiment of a guide wire of the present invention.
Figure 2:
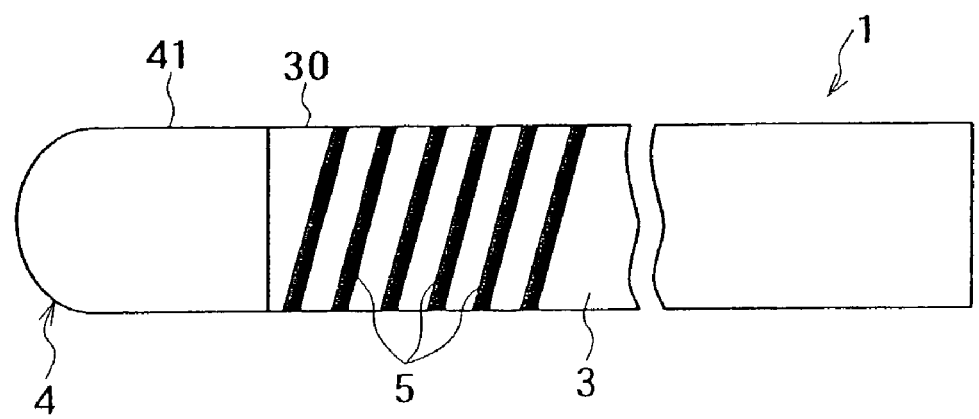
FIG. 2 is a side view of the guide wire shown in FIG. 1

FIGS. 1 and 2 illustrate a first embodiment of a guide wire. For purposes of convenience of description, the right side and the left side in FIGS. 1 and 2 are referred to as the "proximal end side" and "distal end side" respectively.

Referring to FIG. 1, a guide wire 1 according to a first embodiment includes a linear core member 2 and a resin layer or cover layer 3. The resin layer or cover layer 3 is formed to cover at least part of the core member 2.

The core member 2 extends nearly over the entire length of the guide wire 1 and includes a main body portion 22 corresponding to a main body portion of the guide wire 1 and a taper portion 24 positioned at the distal end side of the guide wire 1. The main body portion 22 has a substantially constant diameter, while the taper portion 24 is tapered such that the outer diameter of the taper portion 24 is gradually reduced in the direction toward the distal end.

The taper portion 24 is advantageous in gradually increasing the flexibility of the core member 2, and thus the guide wire 1, in the direction toward the distal end from the vicinity of the boundary between the main body portion 22 and the taper portion 24. This thus helps improve the operation and safety at the time of insertion of the guide wire 1 in a living body.

The outer diameter of the main body portion 22 of the core member 2 is not particularly limited, but is preferably in the range of about 0.3 to 1.0 mm, more preferably about 0.4 to 0.7 mm.

The length of the taper portion 24 can vary depending on the application and/or the kind of guide wire 1. The length of the taper portion is thus not particularly limited, but may be, for example, in the range of about 10 mm to 300 mm.

The core member 2 is made from a metal material or a resin material having a relatively high rigidity. Examples of the metal material include stainless steels, superelastic alloys (pseudo-elastic alloys) such as a Ni—Ti based alloy, a Ni—Al based alloy, and a Cu—Zn based alloy, and cobalt based alloys such as a Co—Ni—Cr—Fe based alloy.

The outer peripheral surface of the core member 2 may be subjected to a treatment capable of enhancing the adhesion on the resin layer 3. Examples of the treatment include a treatment for increasing the surface roughness of the outer peripheral surface of the core member 2 (for example a physical treatment such as a surface coarsening treatment, a chemical treatment using chemicals and a heat-treatment), or a treatment for providing an adhesive layer between the resin layer 3 and the core member 2.

The outer peripheral surface of the core member 2, except for the distal end portion, is covered with the resin layer 3. The resin for forming the resin layer 3 is not particularly limited, but may be selected from polyurethane, a polyolefine such as polyethylene, polypropylene, or ethylene-propylene copolymer, a fluorocarbon resin such as polytetrafluoroethylene, a polyester such as polyethylene terepthalate, polyvinyl chloride, polyamide, polyimide, ethylenevinyl acetate copolymer, ethylene-ethylene acrylate copolymer, ABS resin, AS resin, butadiene-styrene copolymer, polyisoplene, and polybutadiene. These resins may be used singly or in a combination of two or more kinds. Considered from the standpoint of flexibility and adhesion on the core member 2, a resin material having a relatively high flexibility such as polyurethane is preferable.

A color developing agent allowed to develop a color by irradiation with laser light and a contrast agent composed of a powder of a metal oxide are added to the resin material forming the resin layer 3. This color developing agent and the contrast agent will be more fully described below.

Color Developing Agent

The color developing agent used herein is not particularly limited so long as it develops a color by irradiation with laser light. By way of example, the color developing agent may be selected from inorganic materials such as mica, titanium oxide, and a compound thereof, and various kinds of organic color developing agents.

For example, the use of mica as the color developing agent is advantageous in that mica can sufficiently develop a color even if only a small amount of mica is added to the resin material for forming the resin layer 3. In addition, mica substantially does not cause any projection and/or any recess in the color developing portion. Accordingly, the use of mica is effective to suppress a change in color tone of a non-color developing portion because the amount of mica added thereto can be relatively small.

Examples of the color developing agent containing mica include mica belonging to the biotite series, mica belonging to the muscovite series, synthetic mica, a composition of mica, titanium oxide, silicon oxide and tin oxide doped with antimony oxide, a composition of mica and tin oxide doped with antimony oxide, a composition of mica and titanium oxide, a composition of mica, titanium oxide and iron oxide, and a composition of mica and iron oxide. These materials may be used singly or in a combination of two or more kinds.

It is to be noted that the term "color development" used herein refers to not only the specifically-defined "color development" but also various perceivable coloring phenomena such as "discoloration", "decolorization", and "fading".

The content of the color developing agent in the resin layer 3 varies depending on the kind of color developing agent, and the composition and characteristics (particularly color tone) of the resin material. However, to allow the color development agent to develop a color that is neither too much nor too little, the content of the color developing agent is preferably in the range of about 0.01 to 10 wt %, more preferably about 0.1 to 2 wt %. If the content is less than about 0.01 wt %, color developing may become insufficient. The color tone and the intensity of color development after irradiation with laser light can be adjusted by specifying the content of the color developing agent generally within the above range.

It is preferable to evenly mix the color developing agent in the resin layer 3, although it may be locally distributed, for example on the outer surface side of the resin layer 3.

Contrast Agent Composed of Powder of Metal Oxide

The contrast agent composed of a powder of a metal oxide is exemplified by an agent having a contrasting function to X-rays, for example an X-ray opaque material such as barium sulfate, barium carbonate or bismuth oxide. Among these, barium sulfate or bismuth oxide is preferable. These metal oxides may be used singly or in a combination of two or more kinds (particularly by mixing thereof).

As compared with a contrast agent composed of a metal powder, the contrast agent composed of a powder of a metal oxide has a number of advantages. As will be described later, the visible marker 5 is formed by irradiating a desired surface portion of the resin layer 3 with laser light. In this laser irradiation process, if the contrast agent is composed of a metal powder, the agent is liable to be altered, for example oxidized by heat generation due to irradiation with laser light. On the other hand, if the contrast agent is composed of a powder of a metal oxide, the agent is little altered because the agent is originally composed of the metal oxide. Further, the agent does not tend to cause spark and thereby heat generation due to the spark at the time of irradiation with laser light. Accordingly, the use of the contrast agent composed of a powder of a metal oxide is preferable in broadening the degree of freedom in selection of the kind of laser light and the irradiation intensity (energy) thereof, to better clarify the color development of the color developing agent (for example increase the contrast of the developed color), thereby improving the visibility of the visible marker 5.

The average particle size of a powder of a metal oxide used for the contrast agent is not particularly limited. From the standpoint of the dispersability of the powder of a metal oxide, the average particle size is preferably in a range of about 1 to 10 μm, more preferably about 2 to 4 μm.

The content of the contrast agent composed of a powder of a metal oxide in the resin layer 3 varies depending on, for example, the kind of the metal oxide. To allow the agent to exhibit the contrasting function neither too much nor too little, content of the contrast agent composed of a powder of a metal oxide in the resin layer is preferably in a range of about 30 to 80 wt %, more preferably about 50 to 80 wt % on the basis of the whole weight of the resin layer 3. If the content of the contrast agent is less than about 30 wt %, the contrasting function of the resin layer 3 may become insufficient, whereas if the content of the contrast agent exceeds 80 wt %, the mixing of the contrast agent in the resin 3 may become difficult. The contrasting function (contrastability) of the resin layer 3 can be adjusted by appropriately specifying the kind of contrast agent and appropriately selecting the content of the contrast agent generally within the above range.

The contrast agent composed of a powder of a metal oxide is preferably evenly mixed in the resin layer 3, although it may be locally distributed, for example on the outer surface side or on the inner side (core member 2 side) of the resin layer 3. The content of the contrast agent composed of a powder of a metal oxide in the resin layer 3 may be nearly equalized or be partially unequalized along the longitudinal direction of the guide wire 1.

The contrast agent in the resin layer 3 is not limited to be configured so as to form the contrast under X-ray fluoroscopic guidance, but may be configured so as to confirm the position thereof under CT scan guidance, MRI guidance, or the like.

Contrasting Portion

The guide wire 1 has, at the distal end portion of the core member 2, a contrasting portion 4 (corresponding to a second resin layer 32 to be described later) having an X-ray contrasting function (contrastability) higher than that of the resin layer 3. The contrasting portion 4 is made from a resin containing a contrast agent composed of, for example, a metal powder.

The resin for forming the contrasting portion 4 covers the distal end portion of the core member 2. The resin may be selected from those used for forming the resin layer 3. To be more specific, the resin for forming the contrasting portion 4 may be the same kind of resin as that used to form the resin layer 3, although it is preferably a resin (soft resin) having a flexibility higher than that of the resin forming the resin layer 3.

The boundary portion between the resin layer 3 and the contrasting portion 4 has a two-layer structure. More specifically, at the boundary portion, the thickness of the resin layer 3 is gradually decreased toward the distal end, whereas the thickness of the resin forming the contrasting portion 4 is gradually increased toward the distal end. As a result, the gradually increased portion of the contrasting portion 4 overlaps the gradually decreased portion of the resin layer 3, to form an overlapping portion 33. With this configuration, if the resin forming the resin layer 3 is different in characteristics, such as flexibility, from the resin forming the contrasting portion 4, it is possible to moderate the difference in characteristics between both the resins in the longitudinal direction while also improving the adhesiveness between the resins and hence inhibiting or preventing peeling or the like between the resins. As shown in FIG. 1, at least part of the overlapping portion 33 is preferably positioned on the taper portion 24 of the core member 2.

The contrast agent added in the resin for forming the contrasting portion 4 may be composed of a metal powder, for example tungsten or a noble metal such as gold or platinum. A preferred material is tungsten.

As shown in FIG. 1, the contrasting portion 4 is formed on the distal end side from the resin layer 3. The outer surface 41 of the contrasting portion 4 forms a continuous outer surface to the resin layer 3, substantially without a stepped portion. To improve the safety of the guide wire 1, the distal end of the contrasting portion 4 is rounded as shown in FIGS. 1 and 2.

Because the visible marker 5 formed by irradiation with laser light is not provided on the contrasting portion 4 (i.e., is axially spaced from the contrasting portion 4), the contrasting portion 4 is not as liable to experience problems associated with alternation (for example oxidation), spark, and the like due to irradiation with laser light. Accordingly, a metal powder which exhibits a high contrastability can be used as the contrast agent added to the resin for forming the contrasting portion 4. It is also to be noted that the contrasting portion 4 may further contain the above-described contrast agent composed of a powder of a metal oxide.

The content of the contrast agent in the contrasting portion 4 varies depending on, for example, the kind of contrast agent, but in general it is preferably in a range of about 30 to 80 wt %, more preferably about 50 to 80 wt %. If the content of the contrast agent is less than about 30 wt %, the contrasting function of the contrasting portion 4 may become insufficient, whereas if the content of the contrast agent is more than about 80 wt %, the mixing of the contrast agent in the resin may become difficult. The contrasting function (contrastability) of the contrasting portion 4 can be adjusted by appropriately specifying the kind of contrast agent and appropriately selecting the content of the contrast agent generally within the above range.

Although the resin layer 3 has, as described above, contrastability by adding the contrast agent composed of a powder of a metal oxide thereto, there may oftentimes be situations in which it is desired to confirm the position of the distal end portion of the guide wire 1 while being distinguished from other positions. In such a case, it may be advantageous to provide the contrasting portion 4 with a contrastability stronger than that of the resin layer 3.

More specifically, in situations where the guide wire 1 is to be inserted to a desired position (target cite) in a biological lumen via an endoscope, even if the guide wire 1 overpasses the range observable by the endoscope and advances in a peripheral lumen, the position of the distal end portion (contrasting portion 4) of the guide wire 1 can be surely confirmed under X-ray fluoroscopic guidance. Accordingly, the distal end of the guide wire 1 can be surely introduced to the target cite.

The contrasting portion 4 is not limited to be configured so as to form the contrast under X-ray fluoroscopic guidance, but may be configured to permit confirmation of the position thereof under CT scan guidance, MRI guidance, or the like.

Color Developing Portion (Visible Marker)

The visible marker 5 is provided as the color developing portion at a specific location of the outer surface 30 of the resin layer 3. As shown in FIG. 2, the visible marker 5 in this embodiment is provided on the distal end side of the guide wire 1, more specifically in the vicinity of the distal end portion of the resin layer 3. The method of forming the visible marker 5 will be described later.

The shape and dimension of the visible marker 5 are not particularly limited. In the configuration shown in FIG. 2, the visible marker 5 is formed to possess a spiral shape. In the example where the visible marker 5 is formed to have a spiral shape (or an annular shape), the visible marker 5, having a configuration in which spiral lines each having a width ranging from 1 to 10 mm are arranged with a pitch ranging from 1 to 10 mm, may be provided in a range of 3 to 50 cm in the longitudinal direction of the guide wire 1.

The shape of the visible marker 5 is not limited to a spiral shape or an annular shape, but may be any visible shape, for example a linear shape, a corrugated shape, a polka-dot pattern, a grid pattern and a network pattern, and further a numerical number, a letter, a sign, and a scale. To improve the positional confirmation, the visible marker 5 may have a combination of two or more kinds of different patterns, for example a combination of a spiral pattern and an annular pattern.

In the configuration shown in FIG. 2, the visible marker 5 is provided on a portion in the longitudinal direction of the resin layer 3. However, the visible marker may be provided to extend over the entire length of the resin layer 3.

To confirm the movement of the guide wire 1 through an endoscope, the color of the visible marker 5 should be examined in combination with the color of the resin layer 3 (the color of the non-color developing portion). For example, if the color of the visible marker 5 is white or yellow and the color of the resin layer 3 is black, the difference in brightness between these colors is relatively large. That is the contrast between the two colors is relatively high. In this case, the visibility of the visible marker 5 becomes desirably relatively high. Similarly, if the colors of the visible marker 5 and the resin layer 3 are in a complementary relationship, the visibility of the visible marker 5 becomes desirably relatively high. Such a color of the visible marker 5 is determined mainly depending on the kind, characteristics, and content of the color developing agent contained in the resin layer 3. It is preferable that the combination of both of the colors of the visible marker 5 and the resin layer 3 be selected as a combination allowing emergence of a clear contrast therebetween, for example a combination of black or dark color (charcoal grey, dark brown, dark blue, or violet) and yellow, yellowish green, or orange, or a combination of blue and red, orange, or pink. Alternatively, the combination of both of the colors of the visible marker 5 and the resin layer 3 may be a combination of colors which are in the same color series but different in color intensity from each other, for example a combination of dark blue and light blue, or a combination of reddish-brown and pink.

The method of forming the visible marker 5 will be described below. The visible marker 5 is formed by imparting energy to a desired position on the outer surface 30 of the resin layer 3 containing the color developing agent, thereby allowing the color developing agent at the desired position to develop a color by the energy. The way for imparting energy to a desired position is preferably a method involving irradiating the desired position with laser light, but other methods are also possible, for example irradiating the desired position with ordinary light (visible light) condensed by a lens. Hereinafter, the laser irradiation method will be described as one example of the way of imparting energy.

The kind of laser light used herein is appropriately determined in accordance with the kind of color developing agent, but in general it may be selected from near-infrared laser light such as Nd-YAG laser light, far-infrared laser light such as $CO_2$ laser light, and excimer laser light.

The Nd-YAG laser light is near-infrared laser light having a wavelength of 1.06 μm, which can be obtained by irradiating a YAG (yttrium-aluminum-garnet) lot with light emitted from an arc lamp.

The $CO_2$ laser light is far-infrared laser light having a wavelength of 10.6 μm, which can be obtained by pumping with a high frequency (RF) and a high voltage (TEA) applied to a tube filled with $CO_2$ mixed gas.

With respect to the irradiated amount of laser light, in the case of the Nd-YAG laser light, it is preferable to set energy outputted from the energy source in a range of about 1.8 to 2.0 kW.

The laser irradiation system used herein is not particularly limited, and may be any one of the known systems, for example a scanning type system, a dot type system, or a mask type system. The scanning type system is configured such that laser light emitted from an oscillator is scanned in the X-Y direction by two rotating mirrors and is condensed through a lens to irradiate a desired portion. The dot-type system is configured such that laser light is tuned to a polygonal mirror rotated at a high speed to irradiate a desired position. The mask type system is configured such that laser light passes through a mask having a specific pattern and a condense lens to irradiate a desired position.

With the guide wire 1 of the present invention, the above-described way of imparting energy (by irradiation with laser light) is used to impart energy to a desired position on the outer surface 30 of the resin layer 3 containing the color developing agent, thereby heating the color developing agent at the specific position. This allows the color developing agent at the specific position to develop a color to form the visible marker 5 at the desired position.

Coating on Outer Surface

The outer surface of the guide wire 1 is preferably covered with a hydrophilic lubricating coating and/or a hydrophobic lubricating coating. For example, an outer surface portion on the distal end side from a longitudinally intermediate portion of the taper portion 24 of the core member 2 is covered with the hydrophilic lubricating coating, and the remaining outer surface portion on the proximal end side from the intermediate portion of the taper portion 24 is covered with the hydrophobic lubricating coating.

The hydrophilic coating formed on the distal end side of the guide wire 1 becomes wet in a living body to smoothen or improve the sliding motion of the distal end side of the guide wire 1, thereby allowing the guide wire 1 to be smoothly and safely inserted in the living body.

The hydrophobic coating formed on the proximal end side of the guide wire 1 is effective to lower the sliding resistance of the proximal end side of the guide wire 1 against a lumen in which the guide wire 1 is to be inserted, for example a lumen of a catheter or a lumen of an endoscope. This thus improves the guide wire 1 in terms of its operation during in insertion or removal.

The boundary between the portion covered with the hydrophilic lubricating coating and the portion covered with the hydrophobic lubricating coating is positioned on the intermediate portion of the taper portion 24 in this embodiment. However, it is not limited thereto as it may be positioned at an arbitrary point between the proximal end and the distal end of the taper portion 24, or may be at any point out of the taper portion 24.

The boundary between the portion (on the distal end side) covered with the hydrophilic lubricating coating and the portion (on the proximal end side) covered with the hydrophobic lubricating coating is preferably positioned at a point spaced apart 30 to 500 mm from the distal end of the guide wire 1. If the boundary is positioned at a point in this range, it is possible to achieve a relatively good balance between the effects by the hydrophilic lubricating coating and the hydrophobic lubricating coating.

It is possible to form only one of the hydrophilic lubricating coating and the hydrophobic lubricating coating, with the position of such coating not being particularly limited.

The material for forming the hydrophilic lubricating coating may be selected from a cellulose based polymer, a polyethylene oxide based polymer, a maleic anhydride based polymer, and an acrylic amide based polymer. The material for forming the hydrophobic lubricating coating may be selected, for example, as silicone.

FIG. 3 illustrates a second embodiment of the guide wire of the present invention. This second embodiment has a basic configuration similar to that of the first embodiment, and so the following description will focus primarily on the differences associated with the second embodiment. The guide wire 1 according to the second embodiment is the same as the guide wire 1 according to the first embodiment, except that the resin layer 3 in the second embodiment is formed so as to entirely cover the core member 2 and the contrasting portion 4 in the second embodiment has a configuration different from that of the contrasting portion 4 in the first embodiment.

The contrasting portion 4 of the guide wire 1 according to the second embodiment is composed of a metal member 42 having a contrasting function. The metal member 42 surrounds at least part of a taper portion 24 of the core member 2. As shown in FIG. 3, the metal member 42 is formed to possess a coil shape, although it may be formed to possess other shapes such as a ring shape. In particular, the metal member 42 may be composed of a plurality of ring-shaped metal member parts adjacently arranged in the longitudinal direction of the core member 2.

The metal member 42 is made from, for example, tungsten or a noble metal such as gold or platinum. Among these examples of materials, tungsten is preferred.

The distal end portion of the guide wire 1 provided with the metal member 42 exhibits a good contrasting function.

According to this embodiment, because the resin layer 3 is formed to substantially cover the entire length of the core member 2 from the proximal end to the distal end of the core member 2, a color developing portion such as a visible marker 5 can be formed even on the outer surface of the contrasting portion 4.

Figure 4:
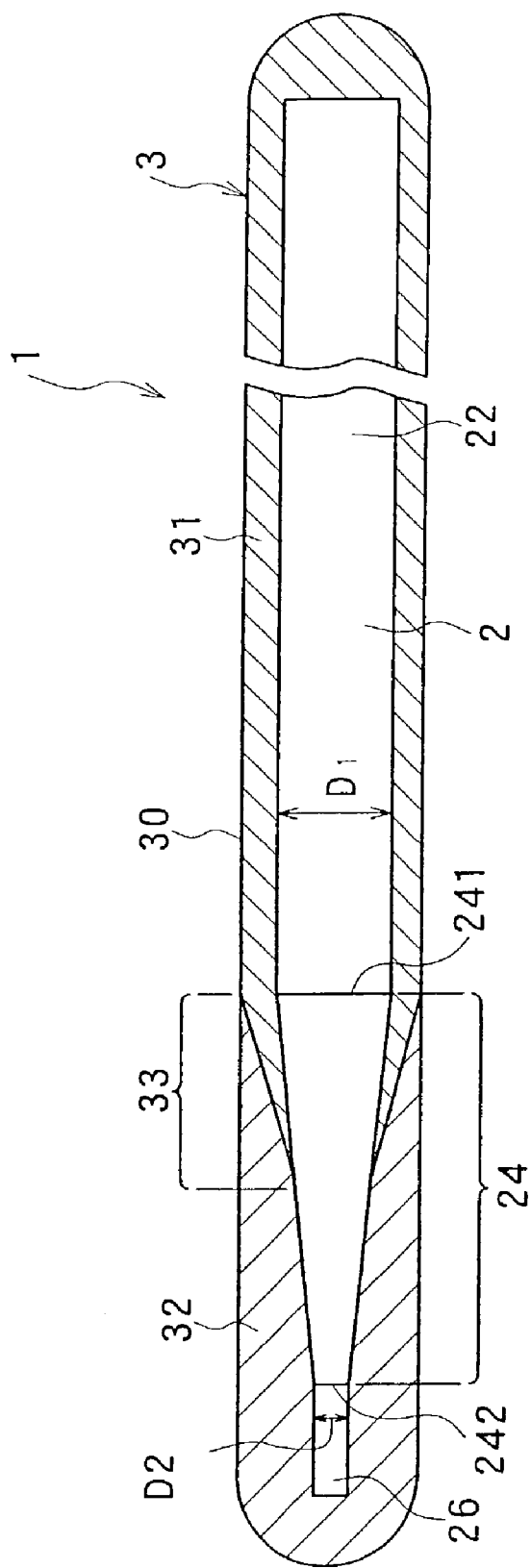
FIG. 4 is a vertical cross-sectional view of a third embodiment of the guide wire of the present invention.
Figure 5:
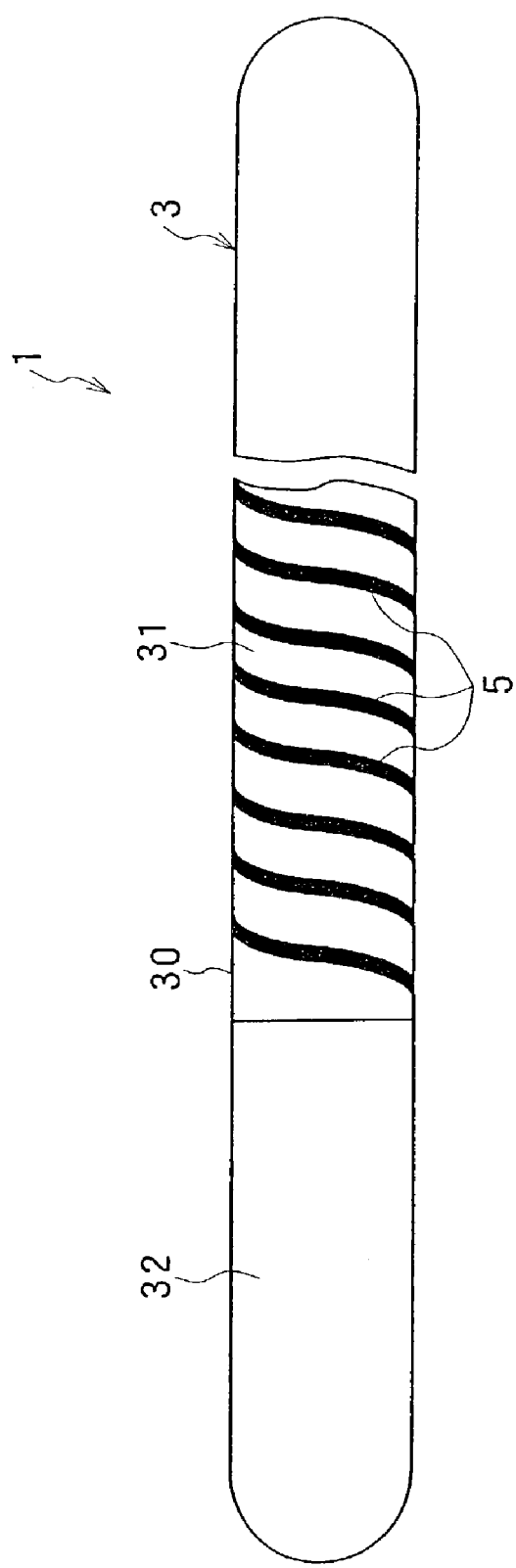
FIG. 5 is a side view of the guide wire shown in FIG. 4.

FIGS. 4 and 5 depict a third embodiment of the guide wire. The third embodiment has a basic configuration or construction similar to that of each of the first and second embodiments described above and so a detailed description of those features and characteristics which are similar to those associated with the first two embodiments will not be repeated. Instead, the following detailed discussion will highlight differences between the third embodiment shown in FIGS. 4 and 5 and the earlier described embodiments.

Referring to FIG. 4, the guide wire 1 according to this embodiment includes a linear core member 2 and a cover layer 3, with the cover layer 3 being formed to cover the outer periphery of the core member 2. The core member 2 extends nearly over the entire length of the guide wire 1. The core member 2 includes a main body portion 22 corresponding to a main body portion of the guide wire 1, a taper portion 24 positioned on the distal end side of the guide wire 1, and a small-diameter portion 26 positioned at the distal end of the taper portion 24. The main body portion 22 possesses a nearly constant outer diameter, the taper portion 24 possesses an outer diameter gradually reduced in the direction toward the distal end (i.e., the taper portion 24 is tapered toward the distal end), and the small-diameter portion 26 has a nearly constant outer diameter.

The taper portion 24 on the core member 2 is advantageous in facilitating a gradual increase in the flexibility of the core member 2, and thus the guide wire 1, in the direction toward the distal end from the vicinity of the boundary (proximal end 241 of the taper portion 24) between the main body portion 22 and the taper portion 24. This thus helps improve the operation and safety at the time of insertion of the guide wire 1 in a living body.

The small-diameter portion 26 at the distal end of the taper portion 24 contributes to lengthening the flexible portion at the distal end of the guide wire 1 so that the distal end portion of the guide wire 1 is more flexible.

The outer diameter $D_1$ of the main body portion 22 of the core member 2 (i.e., the outer diameter of the proximal end 241 of the taper portion 24) is not limited to any particular value, but is preferably in a range of about 0.3 to 1.0 mm, more preferably about 0.4 to 0.7 mm.

The outer diameter $D_2$ of the small-diameter portion 26 of the core member 2 (i.e., the outer diameter of the distal end 242 of the taper portion 24) is also not limited to any particular value, although it is preferably in a range of about 0.05 to 0.3 mm, more preferably about 0.1 to 0.2 mm. Although the outer diameter of the small-diameter portion 26 is nearly constant in this illustrated embodiment, it is not limited in this regard as it may be gradually reduced in the direction toward the distal end.

Depending upon the application and kind of guide wire, the length of the taper portion 24 may vary or be appropriately selected. Thus, while the length of the taper potion 24 is not necessarily limited, it is preferably in a range of about 10 to 300 mm, more preferably about 30 to 250 mm.

The length of the small-diameter portion 26 is also not particularly limited, but is preferably in a range of about 0 to 100 mm, more preferably about 10 to 50 mm.

The small-diameter portion 26 may be replaced with a small-piece portion having a flat-plate shape (strip shape), a prism shape, or the like. The distal end of the small-diameter portion 26 may be provided with an expanded-diameter portion, such an expanded-diameter portion is preferably formed by partially enlarging the diameter of the core member 2 and rounding the enlarged portion as a whole. Alternatively, the expanded-diameter portion may be formed by inserting (mounting) an X-ray opaque ring or coil around the small-diameter portion 26. The small-piece portion having a flat-plate shape helps make the distal end portion of the guide wire 1 more flexible.

The core member 2 is covered with the cover layer (resin layer) 3. The resin layer 3 includes a first resin layer 31 and a second resin layer 32, with the second resin later 32 being positioned on the distal end side from the first resin layer 31. The material forming the second resin layer 32 is preferably higher in flexibility than the material of which the first resin layer 31 is formed.

The first resin layer 31 contains a color developing agent and a contrast agent composed of a powder of a metal oxide, each of which is the same as that described in connection with the first embodiment. The added amounts of these agents and the effects obtained by the addition of these agents are the same as those described above in connection with the first embodiment.

The second resin layer 32 preferably contains a contrast agent which may be at least one of the above-described contrast agents composed of a powder of a metal oxide and a contrast agent composed of a metal powder. The metal used for the latter contrast agent may be selected from tungsten and a noble metal such as gold, silver and platinum, with tungsten being a preferable material because of its high contrastability.

The contrastability of the second resin layer 32 can be made higher than that of the first resin layer 31 by using a metal powder as the contrast agent contained in the second resin layer 32 or making the added amount of the contrast agent composed of a powder of a metal oxide in the second resin layer 32 larger than that in the first resin layer 31. In this case, the second resin layer 32 forms the contrasting portion 4 described in the first embodiment.

The first resin layer 31 covers the main body portion 22 of the core member 2 and part of the taper portion 24, and the second resin layer 32 covers a part of the taper portion 24 and the small-diameter portion 26. In this case, the distal end portion of the first resin layer 31 partially overlaps the proximal end portion of the second resin layer 32, with at least part (preferably a half or more) of the overlapping portion 33 (in a range from the proximal end of the second resin layer 32 to the distal end of the first resin layer 31) is positioned on the taper portion 24. With this configuration, at the taper portion 24 whose outer diameter is gradually reduced in the direction toward the distal end, the volume ratio of the relatively flexible second resin layer 32 to the relatively rigid first resin layer 31 becomes gradually large (i.e., the volume of the relatively flexible second resin layer 32 becomes gradually larger. As a result, the guide wire 1 becomes gradually flexible in the direction toward the distal end in cooperation with the characteristic of the taper portion 24 which becomes gradually flexible in the direction toward the distal end.

The proximal end of the overlapping portion 33 is positioned in the vicinity of the proximal end 241 of the taper portion 24, and the distal end of the overlapping portion 33 is positioned on a portion of the taper portion 24, for example in the configuration shown in FIG. 4 on an intermediate portion of the taper portion 24. However, the present invention is not limited in this regard as it may be configured as follows: (1) both the proximal end and the distal end of the overlapping portion 33 are positioned on the taper portion 24, and (2) the proximal end of the overlapping portion 33 is positioned on the proximal end side from the proximal end 241 of the taper portion 24 and the distal end of the overlapping portion 33 is positioned on a portion of the taper portion 24, for example on an intermediate portion of the taper portion 24. Alternatively, the distal end of the overlapping portion 33 may be positioned in the vicinity of the distal end 242 of the taper portion 24 or on the distal end side therefrom.

At the overlapping portion 33, the first resin layer 31 is covered with the second resin layer 32, wherein the thickness of the first resin layer 31 at the overlapping portion 33 is gradually decreased in the direction toward the distal end and the thickness of the second resin layer 32 at the overlapping portion 33 is gradually increased in the direction toward the distal end.

At the overlapping portion 33, the first resin layer 31 and the second resin layer 32 overlap each other, with the thickness of the first resin layer 31 made from the relatively harder resin material being gradually decreased in the direction toward the distal end and the thickness of the second resin layer 32 made from the relatively softer resin material having a higher flexibility than that of the resin material of the first resin layer 31 being gradually increased. Accordingly, the flexibility of the cover layer 3 (i.e., the stacked portion of both layers) at the overlapping portion 33 is gradually increased in the direction toward the distal end. Meanwhile, as described above, by virtue of the taper portion 24, the flexibility of the core member 2 is gradually increased in the direction toward the distal end from the vicinity of the proximal end 241 of the taper portion 24. As a result, it is possible to obtain a combination effect of the gradually increased flexibility of the core member 2 and the gradually increased flexibility of the cover layer 3 at the overlapping portion. This is advantageous in that the flexibility of the guide wire 1 can be gradually changed (i.e., increased) in the direction toward the distal end, particularly at the taper portion 24 and its neighboring region. The guide wire 1 can thus be more flexibly curved, particularly at the taper portion 24 and its neighboring region. In this way, according to the above-described configuration of the overlapping portion 33, it is possible to significantly improve the operation and safety of the guide wire 1 at the time of insertion of the guide wire 1 in a living body via a catheter or the like.

The boundary between the first resin layer 31 and the second resin layer 32 is preferably configured to form a substantially continuous outer surface to the cover layer 3 substantially without a stepped portion. This also helps improve the operation and safety of the guide wire 1 at the time of insertion of the guide wire 1 in a living body via a catheter or the like.

The first resin layer 31 is joined to the second resin layer 32 at the overlapping portion 33 by fusion, adhesive bonding, or the like. In this case, the joint portion (i.e., boundary) between the first resin layer 31 and the second resin layer 32 is not necessarily clearly defined. For example, the resin materials forming the first resin layer 31 and the second resin layer 32 may be mixed with each other in the vicinity of the joint portion between the first resin layer 31 and the second resin layer 32.

The overlapping portion 33 is constructed so that the first resin layer 31 and the second resin layer 32 overlap each other, with the thickness of the first resin layer 31 being gradually decreased in the direction toward the distal end and the thickness of the second resin layer 32 being gradually increased in the direction toward the distal end. Such an overlapping portion 33 exhibits at least two effects. In one respect, as described above, the overlapping portion 33 helps better smoothen the change in characteristics such as flexibility of the guide wire in the longitudinal direction, thereby making it possible to flexibly curve the guide wire. Another effect is that because the area of the joint portion between the first resin layer 31 and the second resin layer 32 can be made relatively wide, the adhesion between the two layers is improved, thereby preventing peeling of one of the first resin layer 31 and second resin layer 32 from the other even if a bending or torsional force is repeatedly applied thereto. This can be attained not only in the case where the resin materials of the first resin layer 31 and the second resin layer 32 are of the same kind, that is have a good adhesion therebetween, but also in the case where the resin materials of the first resin layer 31 and the second resin layer 32 are different from each other in terms of, for example, the kind or in terms of the composition or added amount of additives (for example the color developing agent, the contrast agent, and the plasticizer) in both of the layers.

As described above, the second resin layer 32 in this embodiment is made from a material (relatively soft material) having a flexibility higher than the material forming the first resin layer 31. However, the present invention is not limited in this respect. For example, even if the flexibility of the resin material of the second resin layer 32 is not different from that of the resin material of the first resin layer 31 to a significant extent, but the additives (for example the color developing agent and the contrast agent) in the resin material of the second resin layer 32 are different in amount and property from those in the resin material of the first resin layer 31, the above-described effect can be obtained. That is, even in this case, because the area of the joint portion between the first resin layer 31 and the second resin layer 32 can be made relatively wide, the adhesion between the two layers can be improved to help prevent the peeling of one of the first resin layer 31 and the second resin layer 32 from the other, even if a bending or torsion force is repeatedly applied.

According to this embodiment, the outer diameter of the guide wire 1, that is the outer diameter of the cover layer 3, is configured to be nearly constant over the entire length of the guide wire 1. However, it may be partially changed (particularly gradually reduced in the direction toward the distal end). For example, the outer diameter of the guide wire 1 may be gradually reduced in the direction toward the distal end from an intermediate portion of the main body portion 22, from the vicinity of the proximal end 241 of the taper portion 24, or from an intermediate portion of the taper portion 24.

The resin material for forming each of the first resin layer 31 and the second resin layer 32 is not particularly limited. For example, the resin material may be selected from those used for forming the resin layer 3 described in the first embodiment.

Even if the first resin layer 31 and the second resin layer 32 are made from resin materials of the same kind (for example polyurethane), the respective flexibility of the resin materials of the first resin layer 31 and the second resin layer 32 can be made different from each other by changing the resin characteristics (for example the average molecular weight, that is degree of polymerization, or the added amount of a plasticizer) of one of the resin materials from the other. As one example, the flexibility of the resin material of the second resin layer 32 can be made higher than that of the resin material of the first resin layer 31 by making the average molecular weight of the resin material of the first resin layer 31 larger than that of the resin material of the second resin layer 32.

According to this embodiment, because the cover layer 3 is composed of the combination of the first resin layer 31 made from a relatively harder material and the second resin layer 32 made from a relatively softer material, it is possible to help ensure the flexibility of the distal end portion of the guide wire 1 and thus improve the operation and safety of the guide wire 1 at the time of insertion of the guide wire 1 in a living body. In addition, because the first resin layer 31 occupying most of the outer surface 30 of the guide wire 1 is made from a resin material having a relatively higher hardness (rigidity), it is possible to reduce the sliding resistance of the guide wire 1 against an inner surface such as the lumen of a catheter or the lumen of an endoscope into which the guide wire 1 is to be inserted, thus helping to improve the operation at the time of insertion or removal of the guide wire 1 or at the time of positioning of the guide wire 1.

To help improve the safety of the guide wire 1, the distal end portion of the second resin layer 32 is rounded. Similarly, the proximal end portion of the first resin layer 31 is rounded.

The application or use of the guide wire 1 of the present invention is not particularly limited. For example, the guide wire 1 may be applied as a guide wire used via an endoscope, more specifically a guide wire (transendoscopic guide wire) used to introduce a catheter inserted in a lumen of an endoscope to a target site in a biological lumen or the like.

When the guide wire 1 is used as a transendoscopic guide wire, the visible marker (color developing portion) 5 provided on the outer surface of the guide wire is viewed through the endoscope. The visible marker can be formed by various methods such as a printing method. According to this embodiment, the visible marker may be formed, for example, by allowing a color developing agent to develop a color by irradiation with laser light. In this case, the color developing agent may be added to the resin material of the cover layer 3 of the guide wire 1, particularly the resin material of the first resin layer 31. The details associated with the color developing agent, and the visible marker 5 and the formation method thereof are similar to those previously described above.

The content of the contrast agent in the material of the first resin layer 31 and/or the material of the second resin layer 32 may vary depending on, for example, the kind of contrast agent. To allow the agent to exhibit the contrasting function neither too much nor too little, it is preferably in a range of about 30 to 80 wt %, more preferably about 50 to 80 wt % on the basis of the whole weight of the resin layer 3. If the content of the contrast agent is less than about 30 wt %, the contrasting function of the resin layer 3 may not be sufficient, whereas if the content of the contrast agent is more than about 80 wt %, it may be difficult to mix the contrast agent in the resin 3. According to the present invention, the contrasting function (contrastability) can be adjusted by appropriately specifying the kind of contrast agent and appropriately selecting the content of the contrast agent generally within the above range.

The contrast agent in the first resin layer 31 and/or in the second resin layer 32 is preferably evenly mixed in the resin layer 3. However it may also be locally distributed, for example on the outer surface side or on the inner side (core member 2 side) of the layer.

The content of the contrast agent in the first resin layer 31 and/or in the second resin layer 32 may be nearly equalized or may be partially unequalized along the longitudinal direction of the guide wire 1. In particular, the content of the contrast agent in the second resin layer 32 can be set to be larger than the content of the contrast agent in the first resin layer 31. This makes it possible to more clearly contrast the distal end portion of the guide wire 1 from the remaining portion of the guide wire 1.

In the case where the content of the contrast agent in the first resin layer 31 is nearly equal to that of the contrast agent in the second resin layer 32, because the thickness of the second resin layer 32 is larger than that of the first resin layer 31, the content of the contrast agent per unit length in the second resin layer 32 is larger than that in the first resin layer 31. As a result, the distal end portion (in the vicinity of the taper portion 24 and the small-diameter portion 26) of the guide wire 1, which is positioned in the second resin layer 32, can form the contrasting portion having a higher contrasting function (contrastability) against X-rays or the like. Of course, if the content of the contrast agent in the second resin layer 32 is larger than that of the contrast agent in the first resin layer 31, the distal end portion of the guide wire 1 can form the contrasting portion having an even higher contrasting function against X-rays or the like.

The second resin layer 32 exhibits the contrastability by adding the contrast agent thereto. However, in some cases, it may be desirable to confirm the position of the distal end portion of the guide wire 1 while distinguishing it from other positions. In these cases, it may be advantageous to provide a contrasting portion having a stronger contrastability at the distal end portion of the guide wire 1 which is positioned in the second resin layer 32.

More specifically, when inserting the guide wire (transendoscopic guide wire) 1 to a desired position (target cite) in a biological lumen via an endoscope, even if the guide wire 1 overpasses the range observable by the endoscope and advances in a peripheral lumen, the position of the distal end portion (contrasting portion) of the guide wire 1 can be relatively reliably confirmed under X-ray fluoroscopic guidance. Accordingly, the distal end portion of the guide wire 1 can be more reliably introduced to the target cite.

To give a contrastability (or a higher contrastability) to the distal end portion of the guide wire 1, alternative techniques can e adopted for providing a metal member such as the above-described metal member 42 in the second resin layer 32 (distal end portion of the guide wire 1). Even in this case, the same effect as that described above can be obtained.

Also, in the guide wire 1 according to this embodiment, it is preferable to subject the outer surface 30 of the guide wire 1 to the above-described coating treatment.

According to the guide wire 1 of the present invention, the contrasting portion (the resin layer 3, the first resin layer 31, or the second resin layer 32 containing the contrast agent) is not limited to being configured to form the desired contrast under X-ray fluoroscopic guidance, but may be configured to confirm the position thereof under, for example, CT scan guidance or MRI guidance.

Figure 6:
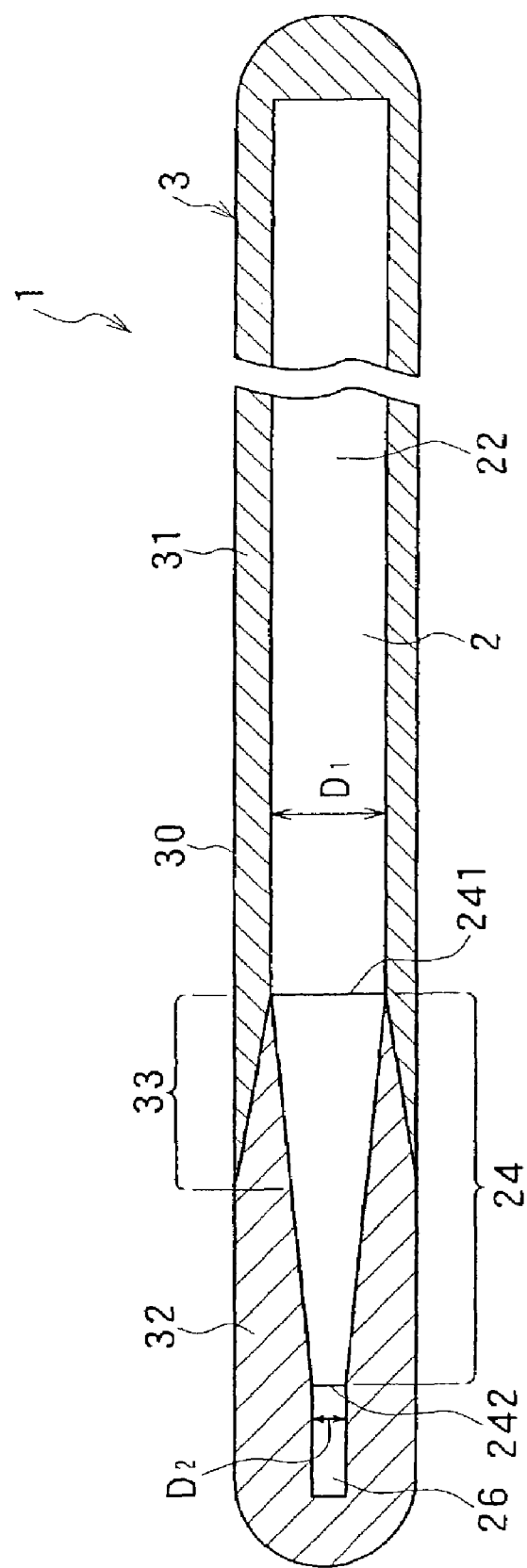
FIG. 6 is a vertical cross-sectional view of a fourth embodiment of the guide wire of the present invention.

FIG. 6 illustrates a fourth embodiment of the guide wire having a basic configuration similar to that of each of the first, second and third embodiments described above. Differences between the fourth embodiment and earlier described embodiments are discussed below.

The guide wire 1 according to the fourth embodiment shown in FIG. 6 is the same as the guide wire 1 according to the third embodiment except that at the overlapping portion 33, the second resin layer 32 is covered with the first resin layer 31. With this version of the guide wire 1, it is possible to obtain effects similar to those associated with the third embodiment of the guide wire 1.

Figure 7:
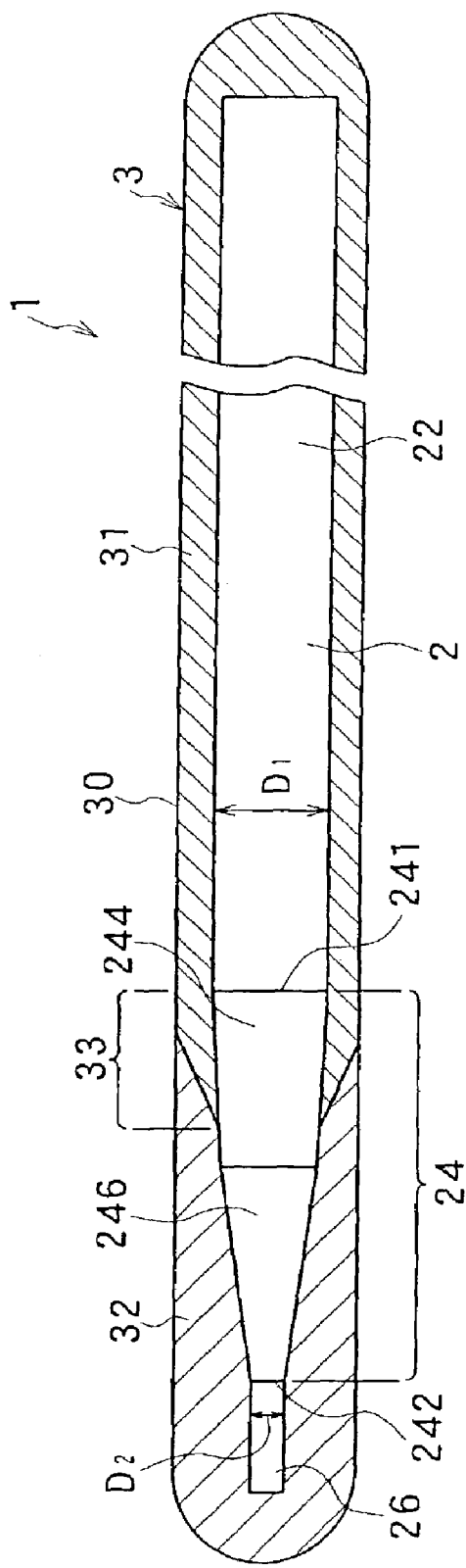
FIG. 7 is a vertical cross-sectional view of a fifth embodiment of the guide wire of the present invention.

FIG. 7 depicts a fifth embodiment of the guide wire of the present invention having a basic configuration similar to that of each of the first to fourth embodiments described above. Differences between this fifth embodiment and earlier described embodiments are discussed below.

The guide wire 1 according to the fifth embodiment embodies one example of a configuration of the taper portion 24 of the core member 2 in which a portion of the taper portion has a taper angle that changes. In this example, the taper portion 24 is composed of a plurality of taper portions having different angles (taper angles). More specifically, as shown in FIG. 7, the taper portion 24 has two taper portions having different taper angles, including a first taper portion 244 on the proximal end side and a second taper portion 246 on the distal end side.

The taper angle of the first taper portion 244 with respect to the center axis of the core member 2 is smaller than that of the second taper portion 246. In other words, the first taper portion 244 is smaller than the second taper portion 246 in terms of the tapering degree in the direction toward the distal end.

Modifications to this embodiment may include a taper portion having a distal taper portion, a proximal taper portion and a nearly constant diameter portion between the distal taper portion and the proximal taper portion.

In the example shown in FIG. 7, at least a part of the overlapping portion 33 at which the first and second resin layers 31, 32 overlap each other is positioned on the first taper portion 244, and the distal end portion of the first resin layer 31 and the proximal end portion of a second resin layer 32 are positioned on the first taper portion 244.

It is to be noted that at least part of the overlapping portion 33 may be positioned on the second taper portion 246, or the overlapping portion 33 crosses the boundary portion between the first taper portion 244 and the second taper portion 246.

Figure 8:
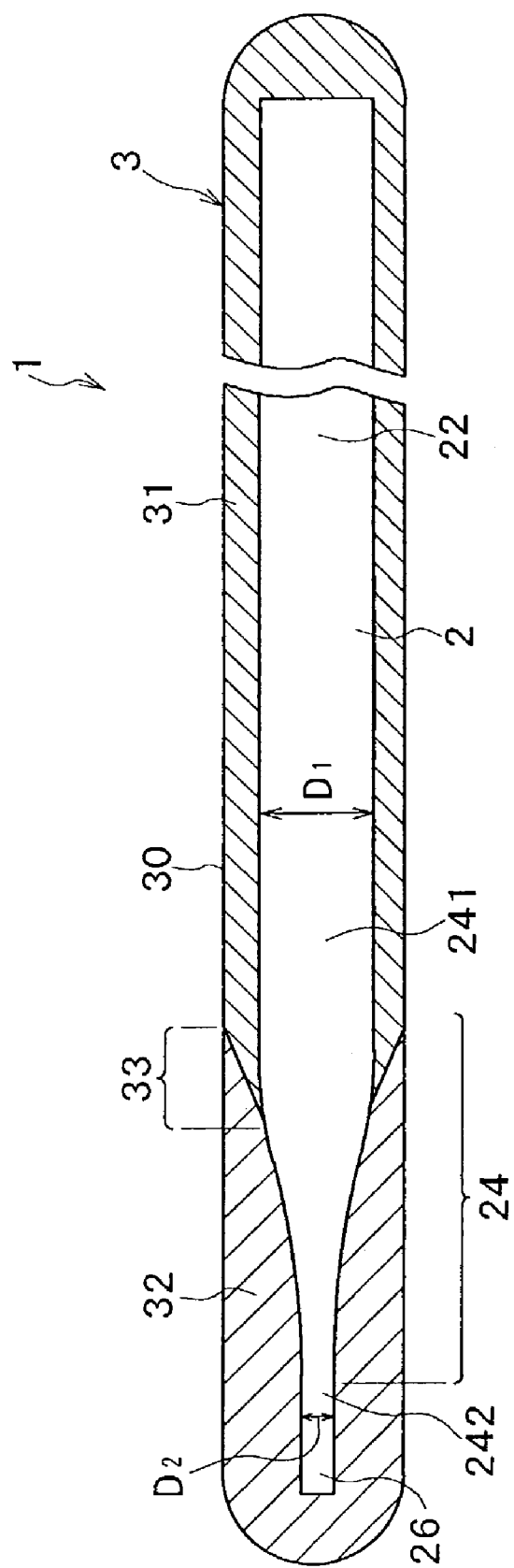
FIG. 8 is a vertical cross-sectional view of a sixth embodiment of the guide wire of the present invention.

FIG. 8 illustrates a sixth embodiment of the guide wire of the present invention having a basic configuration similar to that of each of the first to fifth embodiments described above. Differences between the sixth embodiment and earlier described embodiments are discussed below.

The guide wire 1 according to this sixth embodiment includes another example of a configuration of the taper portion 24 of the core member 2 in which a portion of the taper portion 24 has a taper angle that changes. In this example, the taper angle of the taper portion 24 continuously changes or varies in the direction toward the distal end. More specifically, compared with the configuration of the taper portion in the first embodiment in which the taper portion 24 of the guide wire 1 has a linear contour as viewed from the side, the taper portion 24 embodied in the guide wire 1 shown in FIG. 8 has a curved contour (a generally S-shaped contour) in a side view.

With the configuration shown in FIG. 8, the outer diameter of the taper portion 24 smoothly changes (i.e., is reduced) from the outer diameter $D_1$ of a main body portion 22. More specifically, the reduction ratio of the outer diameter becomes higher at a specific rate to the maximum reduction ratio at the proximal end portion of the taper portion 24, becomes lower at a specific rate in the intermediate portion of the taper portion 24, and becomes lower still at a specific rate in the distal end portion of the taper portion 24 such that the outer diameter is changed in a relatively smoothly continuous manner to the outer diameter $D_2$ of a small-diameter portion 26. With this configuration, it is possible to more reliably prevent the guide wire 1 from being sharply bent (or kinked).

In the embodiment shown in FIG. 8, at least part of the overlapping portion 33 is positioned on the taper portion 24. More specifically, the proximal end portion of the second resin layer 32 is positioned in the vicinity of the proximal end portion of the taper portion 24, and the distal end of the first resin layer 31 is positioned on an intermediate portion of the taper portion 24, preferably at a point offset on the proximal end side from a point where the reduction ratio of the outer diameter is maximized. Of course, the overlapping portion 33 may be positioned at a region of the taper portion 24 different from that described above.

The illustrated configuration of the taper portion 24 having the curved shape in a side view according to the sixth embodiment may be applied to at least one of the first taper portion 244 and the second taper portion 246 in the fifth embodiment of the guide wire.

Figure 9:
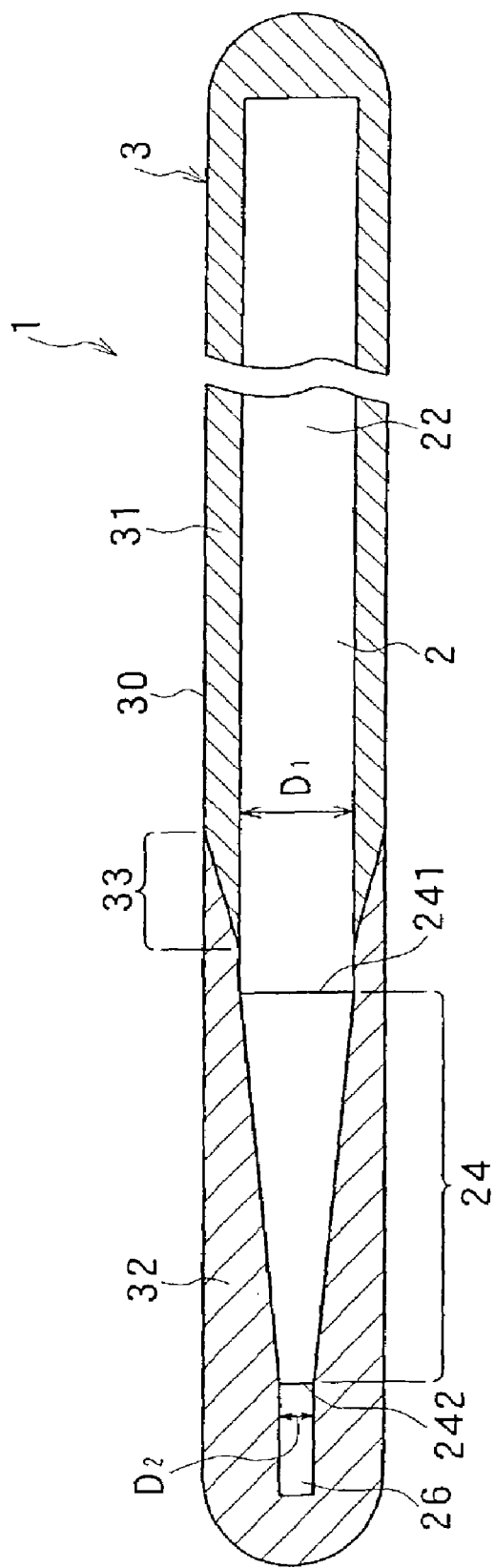
FIG. 9 is a vertical cross-sectional view of a seventh embodiment of the guide wire of the present invention.

FIG. 9 depicts a seventh embodiment of the guide wire of the present invention having a basic configuration similar to that of each of the first to sixth embodiments described above. Differences between this seventh embodiment and earlier described embodiments are discussed below.

The guide wire 1 according to the seventh embodiment includes a linear core member 2 having a main body portion 22 possessing a nearly constant outer diameter and a taper portion 24 provided on the distal end side from the main body portion 22. Like previous embodiments, a cover layer 3 is provided on the outer periphery of the core member 2. The cover layer 3 includes a first resin layer 31 and a second resin layer 32, with the second resin layer being positioned on the distal end side from the first resin layer 31. The second resin layer 32 is made from a material having a flexibility higher than the flexibility of the material forming the first resin layer 31.

At an overlapping portion 33 at which the distal end portion of the first resin layer 31 overlaps the proximal end portion of the second resin layer 32, the first resin layer 31 is covered by the second resin layer 32. Further, at the overlapping portion 33, the thickness of the first resin layer 31 is decreased in the direction toward the distal end and the thickness of the second resin layer 32 is increased in the direction toward the distal end. The overlapping portion 33 is positioned in the vicinity of the distal end of the main body portion 22 of the core member 2.

In the guide wire 1 according to the seventh embodiment, the overlapping portion 33 may be configured in the same manner as that described in the fifth embodiment or the sixth embodiment. Also, in the guide wire 1 according to each of the fifth, sixth and seventh embodiments, the overlapping portion 33 may be configured in the same manner as that described in connection with the fourth embodiment.

Figure 10:
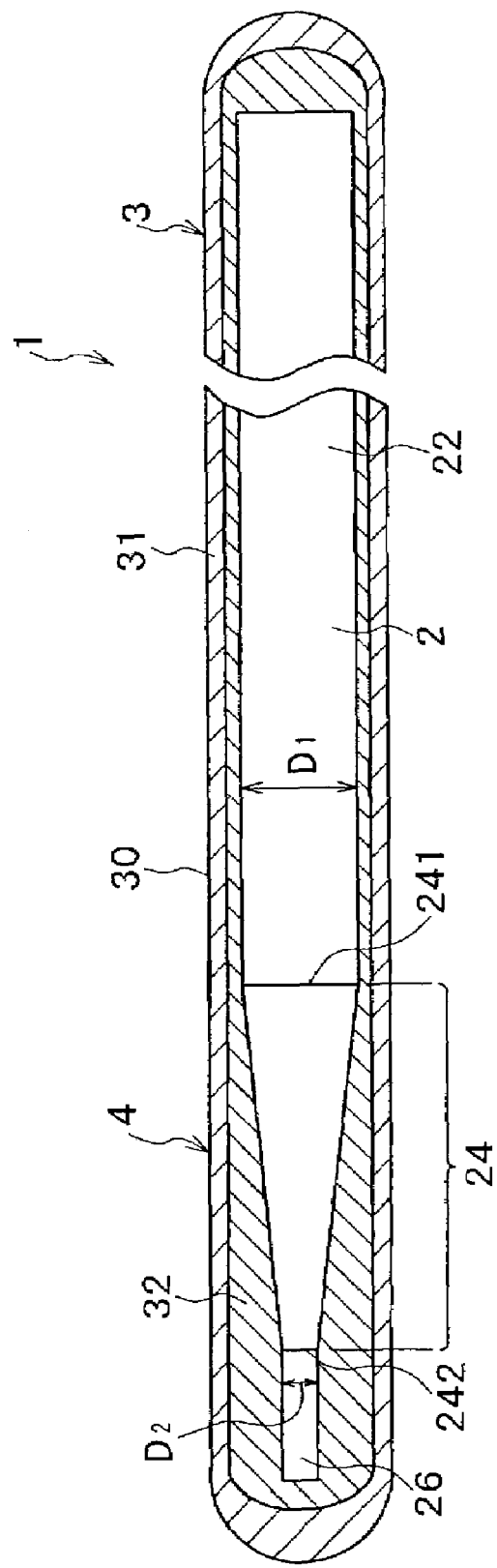
FIG. 10 is a vertical cross-sectional view of an eighth embodiment of the guide wire of the present invention.

FIG. 10 illustrates an eighth embodiment of the guide wire having a basic configuration similar to that of each of the first to seventh embodiments. Thus a detailed description of features associated with the eight embodiment that are similar to those described above in connection with other embodiments will not be repeated. Differences between this eight embodiment and earlier described embodiments are discussed below.

The guide wire 1 according to this eighth embodiment includes a linear core member 2 which has a main body portion 22 possessing a nearly constant outer diameter, and a taper portion 24 provided on the distal end side from the main body portion 22. A cover layer 3 is provided on the outer periphery of the core member 2.

The cover layer 3 has a first resin layer 31 and a second resin layer 32, with the second resin layer 32 being positioned between the core member 2 and the first resin layer 31. In other words, the cover layer 3 is a two-layer stacked construction having the second resin layer 32 as an inner layer and the first resin layer 31 as an outer layer. In this case, both the first resin layer 31 and the second resin layer 32 extend substantially over the entire length of the core member 2.

The thickness of the second resin layer 32 is nearly constant in the main body portion 22, being gradually increased in the direction toward the distal end in the taper portion 24, and is largest in the small-diameter portion 26. The thickness of the first resin layer 31 is nearly constant over the entire length of the guide wire 1. The outer diameter of the second resin layer 32 is nearly constant over the entire length of the guide wire 1, although the outer diameter of the second resin layer 32 in a region on the distal end side from the taper portion 24 may be smaller than that of the second resin layer 32 in a region of the main body portion 22.

The first resin layer 31 contains the same color developing agent and contrast agent composed of a powder of a metal oxide as those described above. In addition, the same visible marker (color developing portion) 5 as that described above is formed at a specific position of the first resin layer 31.

The second resin layer 32 preferably contains a contrast agent whose composition is not particularly limited. In this case, as described above, the contrastability of the taper portion 24 of the guide wire 1 and a portion (for example the small-diameter portion 26) on the distal end side therefrom, that is a contrasting portion 4 corresponding to the thick portion of the second resin layer 32, can be increased by way of the added amount of the contrast agent in the contrasting portion 4 or using a metal powder as the contrast agent in the contrasting portion 4. Alternatively, as described above, a metal member such as the above-described metal member 42 may be provided at the contrasting portion 4.

The second resin layer 32 is preferably made from a material having a flexibility higher than that of the first resin layer 31. With this configuration, the occupied ratio of the second resin layer 32 becomes higher in the taper portion 24 of the guide wire 1 and a portion on the distal end side therefrom, that is the thick portion of the second resin layer 32, thus helping to ensure the flexibility of the distal end portion of the guide wire 1.

Even if the first resin layer 31 and the second resin layer 32 are made from resin materials of the same kind (for example polyurethane), the respective flexibility of the resin materials of the first resin layer 31 and the second resin layer 32 can made different from each other by changing the resin characteristic (for example the average molecular weight, that is degree of polymerization, or the added amount of a plasticizer) of one of the resin materials relative to the other. As one example, the flexibility of the resin material of the second resin layer 32 can be made higher than that of the resin material of the first resin layer 31 by making the average molecular weight of the resin material of the first resin layer 31 larger than that of the resin material of the second resin layer 32.

According to this embodiment, because the first resin layer 31 substantially covers the entire length from the proximal end to the distal end of the core member 2, a color developing member such as a visible marker 5 can be formed even on the outer diameter of the contrasting portion 4, that is on the taper portion 24 of the guide wire 1 and a portion on the distal end side therefrom.

In the embodiment shown in FIG. 10, the entire second resin layer 32 is covered with the first resin layer 31. However, it is to be understood that a portion (for example the distal end portion) of the second resin layer 32 may be exposed from the surface of the guide wire 1.

The second resin layer 32 positioned between the core member 2 and the first resin layer 31 may be present only on the distal end side from the proximal end 241 of the taper portion 24. In this case, the proximal end side from the proximal end 241 of the taper portion 24 is composed of the core member 2 and the first resin layer 31. That is, the cover layer 3 is composed of the first resin layer 31 as the outer layer and the second resin layer 32 as the inner layer on the distal end side from the proximal end 241 of the taper portion 24, and is composed of the first resin layer 31 on the proximal end side from the proximal end 241 of the taper portion 24. In this configuration, the proximal end 241 of the taper portion 24 is taken as the boundary at which the second resin layer 32 is present on the distal end side from the boundary and is absent on the proximal end side from the boundary. However, the present invention is not limited in this regard. For example, an intermediate portion of the taper portion 24 may be taken as the boundary, with the cover layer 3 being composed of the first resin layer 31 as the outer layer and the second resin layer 32 as the inner layer on the distal end side from this boundary, and with the cover layer 3 being composed of the first resin layer 31 on the proximal end side from this boundary.

As shown in FIG. 10, the distal end and the proximal end of the guide wire 1 are each formed into a nearly semi-spherical shape by the first resin layer 31 and the second resin layer 32. The distal end and the proximal end of the core member 2 are each covered with the second resin layer 32 so as to have a smooth surface, with such surface being covered with the first resin layer 31. In addition, at each of the distal end and the proximal end of the guide wire 1, the second resin layer 32 may be formed into a semi-spherical shape, and the first resin layer 31 may be formed into a semi-spherical shape.

Each of the semi-spherical distal end and proximal end of the guide wire 1 may be made from a resin material different from those of the first resin layer 31 and the second resin layer 32. More specifically, each of the distal end and the proximal end of the guide wire 1 may be formed into a semi-spherical shape by using a resin material having a flexibility higher than that of the first resin layer 31. This configuration can help suppress the occurrence of damage of an inner wall of a blood vessel by a portion of the guide wire 1, particularly a portion on the distal end side of the guide wire 1.

While the preferred embodiments of the guide wire of the present invention have been described with reference to the drawings, the present invention is not limited thereto, it being understood that the configuration of each element of the guide wire may be replaced with an arbitrary configuration having the same function, and an arbitrary configuration may be added to each element of the guide wire. In particular, arbitrary features of two of the first to eighth embodiments may be combined with each other.

Also, the application or use of the guide wire of the present invention is not limited to a guide wire (transendoscopic guide wire) used for insertion in a lumen of an endoscope.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
 a linear core member;
 a resin layer positioned about at least a part of said core member, said resin layer including a first resin layer and a second resin layer, with the second resin layer being positioned on the distal end side of said first resin layer, said first resin layer containing a color developing agent adapted to develop a color by irradiation with laser light;

a color developing portion provided on said first resin layer, said color developing portion being formed by color development of said color developing agent and being viewable under endoscopy;

said first resin layer containing an X-ray contrast agent composed of a powder of a metal oxide so that the first resin layer has a contrasting function; and, said second resin layer containing an X-ray contrast agent and having a higher contrasting function compared to the contrasting function of said first resin layer.

2. The guide wire according to claim 1, wherein at least a part of the X-ray contrast agent in the second resin layer is a metal powder.

3. The guide wire according to claim 1, wherein said color developing portion is a visible marker having a portion formed as one of a spiral shape or an annular shape.

4. A guide wire comprising:

a linear core member having a distal end;

the linear core member comprising a main body portion having a substantially constant outer diameter and a taper portion having an outer diameter gradually reduced in a direction toward the distal end of the linear core member;

said taper portion being provided on a distal end side of said main body portion;

a cover layer positioned about an outer periphery of said core member, said cover layer including a first resin layer and a second resin layer, with the second resin layer being positioned on the distal end side of said first resin layer;

said first resin layer containing a color developing agent, said first resin layer also containing an X-ray contrast agent composed of a powder of a metal oxide so that the first resin layer has a contrasting function;

a color developing portion provided at said first resin layer, said color developing portion being formed by color development of said color developing agent and being viewable under endoscopy;

said first resin layer having a distal end portion which overlaps a proximal end portion of said second resin layer to form an overlapping portion; and said second resin layer containing an X-ray contrast agent and having a higher contrasting function compared to the contrasting function of said first resin layer.

5. The guide wire according to claim 4, wherein at least part of said overlapping portion is positioned on said taper portion.

6. The guide wire according to claim 4, wherein said first resin layer possesses a thickness at said overlapping portion that gradually decreases in a direction toward the distal end, and said second resin layer possesses a thickness at said overlapping portion that gradually increases in a direction toward the distal end.

7. The guide wire according to claim 4, wherein a proximal end of said overlapping portion is positioned adjacent a proximal end of said taper portion, and a distal end of said overlapping portion is positioned at a portion of said taper portion.

8. The guide wire according to claim 4, wherein a proximal end of said overlapping portion is positioned on the distal end side from a proximal end of said taper portion, and a distal end of said overlapping portion is positioned on a portion of said taper portion.

9. The guide wire according to claim 4, wherein a proximal end of said overlapping portion is positioned on a proximal end side from a proximal end of said taper portion, and a distal end of said overlapping portion is positioned on a portion of said taper portion.

10. The guide wire according to claim 4, wherein said color developing portion is a visible marker having a portion formed as one of a spiral shape or an annular shape.

11. The guide wire according to claim 4, wherein said taper portion is comprised of a first taper portion and a second taper portion, said first and second taper portions being tapered at different taper angles.

12. The guide wire according to claim 4, wherein said linear core member also includes a small diameter portion having an outer diameter less than the outer diameter of said main body portion.

13. The guide wire according to claim 12, wherein said taper portion is positioned between said small diameter portion and said main body portion.

14. The guide wire according to claim 13, wherein said taper portion is comprised of a first taper portion and a second taper portion, said first and second taper portions being tapered at different taper angles.

15. A guide wire comprising:

a linear core member comprised of a main body portion having a substantially constant outer diameter and a taper portion having an outer diameter gradually reduced in a direction toward a distal end, said taper portion being provided on the distal end side relative to said main body portion;

a cover layer positioned about an outer periphery of said linear core member, said cover layer including a first resin layer and a second resin layer, at least a part of said second resin layer being positioned between said first resin layer and said core member;

said first resin layer containing a color developing agent, said first resin layer also containing an X-ray contrast agent composed of a powder of a metal oxide so that the first resin layer has a contrasting function;

a color developing portion provided on said first resin layer, said color developing portion being formed by color development of said color developing agent and being viewable under endoscopy; and said second resin layer containing an X-ray contrast agent and having a higher contrasting function compared to the contrasting function of said first resin layer.

16. The guide wire according to claim 15, wherein the cover layer comprises an overlapping portion at which an end portion of the first resin layer and an end portion of the second resin layer overlap one another.

17. The guide wire according to claim 16, wherein the end portion of the first resin layer and the end portion of the second resin layer which overlap one another each possess a varying thickness.

18. The guide wire according to claim 15, wherein said color developing portion is a visible marker possessing either a spiral shape or an annular shape.

19. The guide wire according to claim 15, wherein said taper portion is comprised of first and second taper portions that are tapered at different taper angles.

20. The guide wire according to claim 15, wherein said linear core member also includes a small diameter portion having an outer diameter less than the outer diameter of said main body portion, said taper portion being located axially between said smaller diameter portion and said main body portion.

21. A guide wire comprising:

a linear core member;

a resin layer positioned about at least a part of said core member, said resin layer including a first resin layer and a second resin layer, with the second resin layer being positioned on the distal end side of said first resin layer;

said first resin layer having a surface;

a color developing portion provided on said surface of said first resin layer, said color developing portion being formed by irradiation with laser light and being viewable under endoscopy;

said first resin layer containing an X-ray contrast agent;

said second resin layer containing an X-ray contrast agent; and a content of the contrast agent in the first resin aver is larger than a content of the contrast agent in the second resin layer.

* * * * *